United States Patent [19]

Wells et al.

[11] Patent Number: 4,582,904

[45] Date of Patent: * Apr. 15, 1986

[54] AMINE PRODUCTION VIA CONDENSATION REACTIONS USING RARE EARTH METAL HYDROGEN PHOSPHATES AS CATALYSTS

[75] Inventors: James E. Wells, Ardmore, Pa.; Victoria Eskinazi, Cleveland Heights, Ohio

[73] Assignee: Air Products and Chemicals, Inc., Allentown, Pa.

[*] Notice: The portion of the term of this patent subsequent to Jul. 31, 2002 has been disclaimed.

[21] Appl. No.: 568,860

[22] Filed: Jan. 6, 1984

Related U.S. Application Data

[63] Continuation-in-part of Ser. No. 381,232, May 24, 1982, Pat. No. 4,521,600, Ser. No. 381,233, May 24, 1982, Pat. No. 4,501,889, Ser. No. 451,305, Dec. 20, 1982, abandoned, and Ser. No. 451,295, Dec. 20, 1982, Pat. No. 4,446,320.

[51] Int. Cl.$^4$ .................................. C07D 295/02
[52] U.S. Cl. .................................. 544/178; 544/78; 544/352; 544/402; 546/184; 546/248; 564/445; 564/474; 564/479
[58] Field of Search .............. 564/479, 474, 445; 544/352, 102, 78, 402, 178, 358; 546/48, 248, 184

[56] References Cited

U.S. PATENT DOCUMENTS

| | | | |
|---|---|---|---|
| 2,467,205 | 4/1949 | Gresham et al. | 260/268 |
| 2,754,339 | 5/1960 | Herrick | 260/268 |
| 2,985,658 | 5/1961 | Krause | 260/268 |
| 3,172,891 | 3/1965 | Brader, Jr. et al. | 260/268 |
| 3,297,701 | 1/1967 | Brader, Jr. et al. | 260/268 |
| 3,342,820 | 9/1967 | Brader, Jr. | 260/268 |
| 3,541,172 | 11/1970 | Stowe et al. | 260/669 |
| 3,957,900 | 5/1976 | Welsang et al. | 260/681 |
| 4,036,881 | 7/1977 | Brennan et al. | 260/583 |
| 4,049,657 | 9/1977 | Brennan et al. | 260/268 |
| 4,095,022 | 6/1978 | Brennan et al. | 544/87 |
| 4,103,087 | 7/1978 | Brennan | 544/78 |
| 4,117,227 | 9/1978 | Brennan | 544/170 |
| 4,405,784 | 9/1983 | Wells | 544/352 |
| 4,463,193 | 7/1984 | Johnson | 564/479 |

*Primary Examiner*—C. Warren Ivy
*Attorney, Agent, or Firm*—Russell L. Brewer; E. Eugene Innis; James C. Simmons

[57] ABSTRACT

Synthesis of organic amines by condensation of organic hydroxy compound with ammonia or a primary or secondary amine in the presence of a rare earth metal hydrogen phosphate catalyst.

27 Claims, No Drawings

AMINE PRODUCTION VIA CONDENSATION REACTIONS USING RARE EARTH METAL HYDROGEN PHOSPHATES AS CATALYSTS

CROSS REFERENCE TO RELATED APPLICATIONS

This is a continuation-in-part of Ser. No. 381,232, filed May 24, 1982, now U.S. Pat. No. 4,521,600; Ser. No. 381,233, filed May 24, 1982, now U.S. Pat. No. 4,501,889; Ser. No. 451,305, filed Dec. 20, 1982, now abandoned, and Ser. No. 451,295, filed Dec. 20, 1982, now U.S. Pat. No. 4,446,320, the subject matter of all applications being incorporated by reference.

TECHNICAL FIELD OF THE INVENTION

The present invention relates to the preparation of amines by the condensation of an organic hydroxy compound with ammonia or an amine in the presence of a rare earth metal hydrogen phosphate catalyst and is more particularly concerned with the production of amine compounds in enhanced yields and selectivity, and with the ease of such production.

BACKGROUND OF THE PRIOR ART

Amine synthesis via condensation reactions between organic hydroxy compositions and ammonia or an amine resulting in a loss of a molecule of water is well known in the art. Certain such reactions are generally effected in the presence of acidic catalysts. One important area in which such acid catalysis has been employed is in cyclization reactions, as in the synthesis of triethylenediamine (sometimes referred to as TEDA) and its substituted homologues. The following patents are representative of cyclization reactions.

U.S. Pat. No. 2,937,176 discloses the preparation of TEDA by passing an aliphatic amine, such as an alkylene polyamine or alkanolamine over an acidic silica-alumina catalyst at a temperature from 300°-500° C. Diethylenetriamine and N-2-hydroxyethylethylenediamine are noted as being representive reactants for conversion to TEDA.

U.S. Pat. Nos. 2,985,658 and 3,166,558 disclose the preparation of TEDA by effecting condensation of N-aminoethylpiperazine over an acidic silica-alumina catalyst or an activated kaolin catalyst.

U.S. Pat. Nos. 3,172,891; 3,342,820; and 3,297,701 disclose the preparation of TEDA by reacting a hydroxyethoxyethylamine with ammonia or the C-alkyl derivatives of TEDA by reacting hydroxyalkyl alkyl-piperazine derivatives at a temperature from 250°-500° C. in the presence of an aluminum phosphate catalyst. The '820 patent discloses the use of aluminum phosphate containing an alkali metal as a catalyst for the condensation reaction and alleges enhanced activity. Other examples of trivalent metal phosphates having catalytic activity include boron, bismuth and iron phosphates. The '701 patent suggests additional metal phosphate catalysts can be used for effecting the condensation reaction and these metal phosphates include iron phosphate, zinc phosphate, nickel phosphate, copper phosphate, chromium phosphate and cobalt phosphate.

U.S. Pat. No. 4,117,227 discloses the preparation of substituted morpholine compositions by reacting an N-substituted diethanolamine over a phosphorus containing substance. Specific reactions illustrate the conversion of triethanolamine to hydroxyethylmorpholine or dimorpholinodiethylether. Various alkyl and aryl substituted phosphorus and phosphoric acids are alleged as being suited as catalysts and specific catalysts include methylphenylphosphonate, phenylphosphinic acid and ethylphosphonic acid.

U.S. Pat. No. 4,405,784 discloses the preparation of TEDA from hydroxyethylpiperazine and from diethanolamine by effecting a condensation reaction over strontium hydrogen phosphate. Dimethylaminoethylmorpholine was also produced over strontium hydrogen phosphate by condensing dimethylethanolamine with morpholine.

It is also known that TEDA has been produced commercially by the condensation of hydroxyethylpiperazine over strontium hydrogen phosphate at atmospheric pressure more than a year prior to the filing date of the present application but not prior to the filing date of either Ser. No. 381,232 or 381,233.

Intermolecular condensations between a hydroxy compound and ammonia or an amine to form coupled or cyclic compositions are also known. Representative patents showing the preparation of alkyl amines, polyamines and morpholine are as follows:

U.S. Pat. No. 2,754,339 shows the production of aliphatic amines, such as the $C_1$ to $C_6$ alkylamines, typically by reacting an alcohol with ammonia to produce the primary, secondary, or tertiary amine. Generally, silica-alumina, which is high in silica content, is utilized in the reaction. Zinc chloride has also been utilized. One problem experienced with these reactions is that they are thermodynamically limited and a wide product mix is obtained. For example, in the condensation of an alkanol with ammonia, the concentration of the primary, secondary and tertiary amine is fixed; it can be altered only by recycling one or more of the undesirable amines.

U.S. Pat. No. 4,036,811 is representative of techniques for producing polyalkylene polyamines where, for example, monoethanolamine is reacted with ethylenediamine in the presence of a phosphorus-containing composition such as the alkyl and aryl phosphonates. In addition acidic metal phosphates, such as boron phosphate, ferric phosphate, and aluminum phosphate are suggested as being suited for effecting the reaction.

U.S. Pat. No. 3,151,112 and British Pat. No. 1,530,570 show the preparation of morpholine and substituted morpholine compounds by reacting diethylene glycol with ammonia over a hydrogenation catalyst. Hydrogen is included in the atmosphere to maintain reactivity of the catalyst.

U.S. Pat. Nos. 4,103,087; 4,095,022 and 4,049,657 disclose the preparation of a variety of heterocyclic amines by reacting a disubstituted aminoalkanol in the presence of an acid metal phosphate catalyst, e.g., aluminum phosphate or phosphoric acid compound. The '022 patent shows the reaction of a hydroxyalkylmorpholine to produce the bis-morpholino-N-alkyl-ether, the reaction being carried out in the presence of an acid metal phosphate. The '657 patent produces N-aminoalkylpiperazine by reacting piperazine with a primary or secondary aminoalkanol in the presence of a phosphorus-containing substance such as an alkyl or aryl phosphinate or acidic metal phosphate.

SUMMARY OF THE INVENTION

This invention pertains to an improved process for the condensations of (a) an organic reactant containing either a hydroxyl group with (b) a reactant containing an amine hydrogen, or with, ammonia to form a variety of amines or for condensations where both hydroxyl and amine hydrogen are present in the same molecule in which case compositions (a) and (b) are defined by the same formula and then only one of said compositions is required. One of the basic methods comprises a process for the synthesis of an organic amine by the intermolecular condensation of an organic hydroxy composition with ammonia or a primary or secondary amine, such condensation being effected in the presence of a phosphorus-containing compound as a catalyst. The improved process is, in a more specific aspect, a method for effecting the condensation between (a) a hydroxy composition represented by the formula:

$$R(OH)_x$$

where R is saturated aliphatic radical having from 1 to 6 carbon atoms, an olefinic radical having from 3 to 6 carbon atoms, aliphatic ether having from 4 to 8 carbon atoms, or aminoalkyl where the alkyl portion has from 2-6 carbon atoms; and x is 1 when R is methyl and 1 or 2 if R is $C_2$ or greater, and (b) an amino compound represented by the formula:

$$R_1R_2NH$$

where $R_1$ and $R_2$ are each selected from hydrogen, saturated aliphatic radical having from 1 to 4 carbon atoms, an olefinic radical having from 3-7 carbon atoms hydroxyalkyl having from 1 to 3 carbon atoms, aminoalkyl having 2 to 4 carbon atoms; or are combined to form a cyclic group having from 4 to 10 carbon atoms, by utilizing a rare earth metal hydrogen phosphate as a catalyst to effect the condensation reaction.

A second basic method comprises a process for the synthesis of cyclic amines by the intramolecular condensation of a hydroxyl group with an amine hydrogen present on a hydroxyamine compound, such condensation being effected in the presence of a phosphorus-containing compound as a catalyst. The improved process of the invention, in another aspect, involves effecting the formation of cyclic amines by the intramolecular condensation of a hydroxyamine composition represented by the formula:

$$OHR_3NHR_4$$

where $R_3$ is alkyl having 1 to 4 carbon atoms, alkoxy having 2 to 4 carbon atom, or a cyclic group having 4 to 10 carbon atoms and $R_4$ is hydrogen or alkyl having 1 to 4 carbon atoms and utilizing a rare earth hydrogen phosphate as a catalyst in the condensation reaction.

There are significant advantages of using a rare earth hydrogen phosphate as a catalyst for effecting intermolecular or intramolecular condensation reactions with the reactants identified above, and some of the potential advantages include:

an ability to effect efficient condensation of an amine hydrogen with a hydroxy group;
an ability to produce a variety of lower aliphatic and cyclic amines in good selectivity and high yields;
an ability to operate under vapor phase conditions utilizing a heterogeneous catalyst system thereby facilitating production and separation of materials;
an ability to achieve good catalyst life due to substantial insolubility of the catalyst in the reaction medium and due to the ability to maintain gas phase reaction conditions;
an ability to produce unsymmetrical amines, i.e., amines which in the same molecule have different organo radicals, e.g., methylethylamine; and
an ability to produce symmetrical amines, e.g. dimethylamines, trimethylamine without creating a broad product mix;

DETAILED DESCRIPTION OF THE INVENTION

In the condensation of an organic hydroxy composition with an amino composition, both intermolecular condensations and intramolecular condensations, (a reaction occurs between an amino group and a hydroxy group present in the same molecule), can be effected to form a variety of aliphatic and cyclic amines. In intramolecular condensations the compositions which contain both hydroxyl and amino hydrogen functionality, or in which such functionality is generated in situ, tend to form cyclic compositions.

The hydroxy compositions suited for practicing the invention in terms of intermolecular condensations are best represented by the formula $R(OH)_x$ where R is alkyl having from 1 to 6 carbon atoms, an olefinic radical having from 3 to 6 carbon atoms, alkoxy having from 4 to 8 carbon atoms or aminoalkyl where the alkyl portion has from 2 to 6 carbon atoms, and x is 1 when R is methyl, and 1 or 2 if R is $C_2$ or greater. Representative hydroxy compositions where R is alkyl include methanol, ethanol, propanol, butanol the corresponding glycols, such as, ethylene glycol, propylene glycol, butane diol and the like. When R is alkoxy and the organo portion contains ether linkages therein, such examples include methoxyethoxyethanol, ethoxyethanol, ethoxybutanol and diethylene glycol; aminoalkyl compounds include monoethanolamine, diethanolamine and propanolamine. When R is olefinic, such olefinic alcohols suited for practicing the invention include allyl alcohol and diallyl alcohol.

The amino compositions suited for condensation with the above hydroxy composition is represented by the formula $$R_1R_2NH$$

where $R_1$ and $R_2$ are hydrogen, alkyl having from 1 to 4 carbon atoms, an olefinic radical having 3-6 carbon atoms, hydroxyalkyl, where the alkyl portion has from 2 to 6 carbon atoms, alkoxy having from 4 to 8 carbon atoms or $R_1$ and $R_2$ are combined to form a cyclic group which includes heterocyclic groups and cycloalkyl groups $R_1$ and $R_2$ can be alike or different. Representative hydrogen, alkyl and amino compositions suited for condensation with the hydroxy composition include ammonia, methylamine, dimethylamine, ethylamine, diethylamine, propylamine, dipropylamine, allylamine, diallylamine, ethylenediamine and propylenediamine. Representative hydroxyalkylamines include monoethanolamine and propanolamine. Representative ester and cyclic amines include 2-(2 aminoethoxyethanol), piperazine, morpholine, and hydroxyethylpiperazine. As noted in both the formula for the hydroxy and for the amino compositions, the organic portion can be substituted with a variety of groups, particularly hydroxy or amine, and substituted derivatives are included within the terms alkyl, olefinic, etc.

In the reaction between a hydroxy composition of the formula $R(OH)_x$ and an amino compound of the formula $R_1R_2NH$, a single condensation would occur if there was only a single amino hydrogen or a single hydroxy group. A double condensation could occur if the amine were a primary amine or ammonia, and x were 2. But, a double condensation need not occur and that condensation would depend upon the molecular structure. It also follows from the formulas that the hydroxy composition and the amine composition may be one in the same, e.g., a hydroxy substituted amine such as monoethanolamine. Where the hydroxy amine is a short chain, i.e., 2 to 3 carbon atoms, the first reaction may be intermolecular followed by a second intramolecular reaction. For example, one molecule or mole of hydroxy amine, i.e. alkanolamine may react with another molecule or mole of an alkanolamine (one being considered the hydroxy composition and the other the amino composition even though the alkanolamine may be the same composition) through an intermolecular condensation and then that reaction product reacting with itself, thus effecting intramolecular condensation.

The production of cyclic amines can occur by the intramolecular condensation of a hydroxy substituted amine of the formula:

$$OHR_3NHR_4$$

wherein $R_3$ is alkyl having from 1 to 4 carbon atoms, cyclic having from 4 to 10 carbon atoms, alkoxy having from 4–8 carbon atoms, and $R_4$ is alkyl having from 1 to 4 carbon atoms.

Representative hydroxy substituted amines which can cyclize through intramolecular condensation include hydroxyethyl piperazine, 2-(2 aminoethoxyethanol and aminoethylethanol.

The catalysts suited for practicing the invention are the rare earth metal monohydrogen and dihydrogen phosphates. These are conventionally prepared by reacting a hydrogen phosphate precursor with a rare earth metal salt. Typically, an alkali metal or ammonium mono or dihydrogen phosphate is reacted with a water soluble rare earth metal salt, the rare earth metals being those of the tanthanide series. Phosphoric acid can also be used as a hydrogen phosphate precursor. Either the monohydrogen or dihydrogen form is obtained by using the corresponding precursors. The mono hydrogen or dihydrogen form may also be obtained by pH adjustment of the solution with ammonia or acid. U.S. Pat. No. 3,752,878 is representative of disclosure of formation and is incorporated by reference. Suitable rare earth metals (Groups IIIb) include lanthanum, cerium, praseodymium, neodymium, promethium, samarium, thulium, ytterbium, lutetium, and dysprosium and mixtures thereof. Typically, these metals appear as mixtures of rare earth metal salts and a typical catalyst may contain a preponderance (at least 80% by weight) of lanthanum with minor portions of rare earth metals such as neodymium, praseodymium, ytterbium and the like. Lanthanum hydrogen phosphate which is intended to include the lanthanum mixtures of at least 80% by weight lanthanum and in either mono or dihydrogen form are preferred.

While it is the intent in catalyst preparation to produce a monohydrogen or a dihydrogen phosphate, it is more likely that a mixture of products, i.e., monohydrogen, dihydrogen and the metal phosphates exist owing to the complicated dependence on preparation conditions. It is difficult to synthesize, let alone analyze, the end composition to determine if only a single or dihydrogen phosphate component is present. Therefore, for purposes of this invention, the term rare earth metal hydrogen phosphate is intended to include a single product or a mixture of products obtained by contacting a rare earth metal salt with an alkali metal or ammonia monohydrogen or dihydrogen phosphate, or other hydrogen phosphate precursor, the contacting being done with sufficient amount of the alkali metal monohydrogen or dihydrogen phosphate or other hydrogen phosphate precursor to convert substantially all of the rare earth metal salt to either the monohydrogen or dihydrogen phosphate. Usually, this level is from 0.5 to 1.5 moles phosphate salt per mole rare earth metal salt. Preferably the molar ratio is at least 1:1. Under the conditions conventionally used for converting the rare earth metal salts to rare earth monohydrogen and dihydrogen phosphates, it is assumed that at least 50% of the rare earth metal salt is converted when a 1:1 mole ratio of hydrogen phosphate precursor is employed.

The condensation between an amine hydrogen and a hydroxyl group in which there is a resultant loss of a molecule of water, whether the condensation be intermolecular or intramolecular, can be effected at moderate temperatures e.g. 200° C. and up to 420° C. at pressures ranging from subatmospheric to superatmospheric e.g. a range from about 0.1 to 150 atmospheres. In situations where one of the reactants has a high vapor pressure at the temperature utilized in the reaction, it may be preferable to operate under pressure in order to enhance the condensation reaction. For example, it is difficult to condense ammonia with a hydroxy composition except under moderate pressures e.g. 150 psig to 600 psig and above. Temperature is also important in the synthesis. For example, where the condensation reaction proceeds readily, as in the case of many alkylamines, temperatures at the lower end of the range may generally result in higher selectivity. Where the condensation reaction is more difficult, such as in the case of polyamine synthesis, higher temperatures may be required to achieve desired conversion without sacrificing selectivity.

One of the advantages of the catalyst system of this invention is that it is capable of effecting condensation between a hydroxy composition and an amino hydrogen of ammonia or alkyl amine and convert these reactants to a symmetrical or unsymmetrical alkylated amine. Catalysts typically used in the prior art were thermodynamically limited and a fixed product mix usually containing numerous products was obtained. For example, in the production of symmetrical amines, when one uses a rare earth hydrogen phosphate to effect the catalytic amination of methanol with ammonia, it is possible to alkylate and produce a high proportion of monomethylamine which then can further react with additional quantities of methanol to produce dimethylamine, and then further react quantity of methanol to produce trimethylamine. In the prior art a broad mixture of the primary, secondary, and tertiary amines was generated in contrast to the present process and the product mix was changed by altering the composition of the feedstock, e.g. recycling undesired amine. In the production of unsymmetrical amines, i.e., an amine having different organo groups present in the molecule, it was difficult, if not impossible, to produce such compounds with prior art catalysts. With the rare earth hydrogen phosphate catalysts, it is possible to produce the unsymmetrical amines with good selectivity. For example, one can react methanol with ethylamine to produce methylethylamine and then react the methylethylamine with additional methanol to produce dimethylethylamine.

The following specific reactions are provided to illustrate both intermolecular and intramolecular condensations of hydroxy and amino compositions represented by reacting: For convenience dashes have been used to define a range. For example 1–4 means from 1 to 4.

1. Morpholine and a $C_{1-4}$ alkanol such as dimethylethanol or ethanol to produce N-alkyl morpholines.

2. Morpholine and a hydroxy or hydroxyalkoxy-substituted alkylamine, e.g., ethanolamine, dimethylethanolamine or ethoxyethanol to produce N-alkylaminomorpholines.

3. $C_{1-4}$ alkanolamines and ammonia or a primay or secondary $C_{1-4}$ alkylamine, e.g., diethanolamine and methylamine to produce symmetrical and unsymmetrical amines.

4. Diethyleneglycol and a $C_{1-4}$ alkylamine, ammonia or an alkanolamine to produce either an amino substituted alkoxy glycol, morpholine or an N-alkyl morpholine.

5. Allylalcohol and ammonia or a $C_{1-4}$ alkylamine, to produce allylamine or substituted allylamine.

6. $C_{1-4}$ alkyl glycol and ammonia or alkylamine to produce a polyamine.

7. $C_{1-4}$ alkanol and a primary or secondary $C_{1-4}$ alkylamine to produce unsymmetrical alkylamines, e.g., the reaction of diethylamine and methanol or alternatively, dimethylamine and ethanol.

8. Ethylene glycol and piperazine to produce hydroxyethylpiperazine followed by the intramolecular condensation to produce TEDA.

The above two reactions, 4 and 8, illustrate an intermolecular and then an intramolecular condensation.

The quantity of rare earth metal acid phosphate salt used in the condensation reaction can vary widely depending upon the activity of the particular catalyst used and the reactivity of the reactants in the system. In any event, a sufficient amount of catalyst is included in the reaction to be catalytically effective, i.e. an amount which causes the condensation between the hydrogen atom of ammonia or amine with the hydroxyl group on a composition, whether the condensation is inter or intramolecular. In batch reactions the amount ranges from about 0.1 to 25% by weight based upon the combined weights of the hydroxy composition and the amino composition. Within this range, the level of catalyst utilized is empirical, depending upon the reactivity and conditions utilized and the product slate desired. The conditions and catalyst level are adjusted to optimize product conversion selectivity. Generally, at least 90% and preferably 100% by weight of the catalyst (excluding supports) used in the reaction is the rare earth metal hydrogen phosphate.

The reactions can be carried out in batch mode as well as continuous, as for example in a continuous stirred tank reactor or a packed bed reactor. When the reaction is carried out in a packed bed reactor, a GHSV of 500 to 10,000 hr$^{-1}$ is generally used. If the reaction is carried out in an autoclave, the reaction may be carried out in about 1–3 hours. Alternatively, the feed rate may be expressed as an LHSV and such rate is from 0.05-5 hr$^{-1}$. Both GHSV and LHSV are based upon feed rates to the reactor, GHSV is calculated assuming ideal conditions. The precise condition of gas or liquid phase within the reactor is not known and need not be determined to carry out the reaction.

The following examples are provided to illustrate a variety of reactions using the concepts of this invention.

EXAMPLE 1

Catalyst Preparation

The general technique for preparing a variety of rare earth metal hydrogen phosphates was effected by dissolving a preselected quantity (in grams (g)) of rare earth metal nitrate in 500 cc of distilled water. Then, a preselected quantity (in grams (g)) of monobasic or dibasic ammonium phosphate—$(NH_4)_2HPO_4$—was dissolved in a separate vessel containing 500 cc distilled water. Heat was applied to effect dissolution. The two salt solutions were then combined and stirred for about 10 minutes. The temperature was maintained within a range of 40°–60° C. After stirring, the combined solutions were vacuum filtered, and the resulting precipitate washed with distilled water and air dried overnight in a static oven at approximately 110° C. The filter cake was then broken into small ($\frac{1}{8}$th to $\frac{1}{4}$ inch) irregular granules for evaluation. The solution prior to precipitation was measured for solution pH as determined by acid-base indicators. If the pH were greater than 4, it was believed that insufficient hydrogen phosphate source had been reacted to produce a desired catalyst. A solution pH of 1 to 3 was deemed preferable; acid or base was used to adjust solution pH. The surface pH of the catalyst after precipitation was also measured with acid-base indicators.

Specific catalyst systems prepared in accordance with the above-described technique are shown in Table 1, the grams of each salt preceding the formula. It was assumed the ammonium monobasic phosphate gave the corresponding rare earth monobasic phosphate and the ammonium dibasic phosphate gave the rare earth dibasic phosphate.

TABLE 1

| Run | Salt Solution g/type | Phosphate g/type | Surface pH |
| --- | --- | --- | --- |
| 1 | 168 Nd (NO$_3$).5H$_2$O | 80 (NH$_4$)$_2$HPO$_4$ | — |
| 2 | 217 Ce (NO$_3$)$_3$.6H$_2$O | 99 (NH$_4$)$_2$HPO$_4$ | 0.2–1.2 |
| 3 | 415 La (NO$_3$)$_3$.5H$_2$O | 198 (NH$_4$)$_2$HPO$_4$ | 0.2–1.8 |

EXAMPLE 2

Preparation of Triethylene Diamine

The manufacture of triethylenediamine (TEDA) was accomplished by effecting an intramolecular condensation of hydroxyethylpiperazine (HEP) in accordance with the following test procedure:

(a) 20 cc (approximately 6.2 grams) of catalyst were packed into a $\frac{3}{4}$ inch diameter stainless steel reactor;

(b) the reactor was placed in a conventional tube furnace such that the catalyst bed was near the furnace center and therefore could be heated to a constant and uniform temperature;

(c) the catalyst bed temperature was raised to a temperature of from about 340°–400° C. over a period of about 15–30 minutes while a small flow of gaseous nitrogen was maintained through the reactor to aid in the removal of water vapor;

(d) a feed mixture containing HEP and water such that the organic component made up 60% by weight of the mixture was then allowed to flow through the catalyst bed at a rate of about 6.5–7 cc/hr., the nitrogen flow being discontinued during the addition of the feed mixture;

(e) Table 2 sets forth the catalyst, catalyst bed reaction temperature, conversion and yield of specific products produced, either TEDA or piperazine (PIP) based upon feed. Analyses were performed using gas chromatographic techniques.

TABLE 2

| Run | Catalyst | TEDA Yield wt % | PIP Yield wt % | Conversion mole % | T °C. |
|---|---|---|---|---|---|
| 1 | $Nd_2(HPO_4)_3$ | 18.2 | 5.4 | 98.4 | 340 |
| 2 | $Ce_2(HPO_4)_3$ | 32.3 | 8.4 | 99.9 | 340 |
| 3 | $La_2(HPO_4)_3$ | 16.2 | 4.2 | 98.8 | 340 |

Higher selectivity might be produced by operating at higher pressure and lower temperature. Selectivity to TEDA was good.

EXAMPLE 3

Preparation of Catalyst on Alumina Spheres

Prior to charging the reactor of the type used in Example 2, the catalysts of Example 1 Runs 1–3 were deposited upon alumina spheres in the following manner. Several reactor charges of low surface area alumina spheres were prepared by charging each specific catalyst to a jar-mill containing alumina spheres. The weight ratio of catalyst to alumina spheres was about 25 weight parts active catalyst to 75 weight parts alumina powder. The catalyst and alumina spheres were rotated in the jar-mill for several days, and the catalyst forced into the caused to adhere to the surface of the alumina spheres. The resulting product was referred to as a supported catalyst.

EXAMPLE 4

Preparation of Unsymmetrical Alkylamines

Approximately 20 cc of the lanthanum monohydrogen phosphate catalyst from Example 3 supported on alumina were charged to the reactor of the type used in Example 2. In one case, the unsymmetrical amines were prepared by reacting a feed mixture of monoethylamine (EA) and methanol (MEOH), the feed mixture containing one mole of primary amine and one mole of alcohol, respectively. The product obtained was dimethylethylamine (DMEA). The reaction was carried out at one atmosphere pressure and an LHSV of 0.15 hr.$^{-1}$ The temperature of the reaction zone was 350° C. In another case, diethylamine (DEA) was substituted for the monoethylamine and another unsymmetrical amine produced (diethylmethylamine DEMA).

Table 3 sets forth the results for the two reactions utilizing the same catalyst system. Both yield and selectivity are expressed as mole %.

mine was produced. In Run 2 no mono or di alkyl amine was produced.

EXAMPLE 5

Preparation of Methylamines

The synthesis of methylamines was carried out by reacting ammonia and methanol in the presence of $La_2(HPO_4)_3$ of the type synthesized in Example 3 at a temperature of about 350° C. at 1 atmosphere pressure, and a LHSV of 0.15/hr. The mole ratio of ammonia to methanol was 1:1. The results obtained, based upon the methanol in the feed was:

13 mole percent trimethylamine (TMA);
2.8 mole percent dimethylamine (DMA); and
3 mole percent monomethylamine (MA).

The selectivity, based upon the methanol feed, was 69% TMA, 14.9% DMA and 16 mole % MA. The methanol conversion under these conditions was 52 mole %.

EXAMPLE 6

Preparation of N-Allyl Amine

Allyl alcohol and ammonia were reacted over a lanthanum dihydrogen phosphate catalyst in a tubular reactor by first charging approximately 6 cc of the catalyst having a mesh size of approximately 12–18 U.S. standard to the reactor. The catalyst was initially heated in helium to a temperature of about 200° C. Once, at that temperature, ammonia was introduced into the tubular reactor and after about 1½ hours allyl alcohol was introduced downflow. The feed molar ratio of ammonia to allyl alcohol maintained at the time of introduction was approximately 4:1; the reactor pressure was maintained at 450 psig, and the gas hourly space velocity was maintained at about 1,000 hr.$^{-1}$.

Table 4 sets forth conditions of temperature, conversion and selectivity to the allylamine product slate.

TABLE 4

| | ALLYL ALCOHOL-AMMONIA REACTION | | | | |
|---|---|---|---|---|---|
| Temp. °C. | Allyl Alcohol conv. | MAA | DAA | TAA | B—Picoline |
| 220 | 0.85 | 100 | — | — | — |
| 240 | 6.9 | 94 | 2.6 | 1.3 | 2.6 |
| 780 | 8.7 | 87 | 5.1 | 1.7 | 5.5 |
| 300 | 12.9 | 88 | 3.6 | 2.0 | 6.3 |
| 320 | 21.7 | 79.1 | 11.3 | — | 9.6 |
| 340 | 25.1 | 76 | 12.3 | 6.6 | 5.2 |

MAA refers to monoallylamine, DAA to diallylamine, TAA to triallylamine or B-picoline to beta-picoline. Selectivity to monoallylamine is quite high as compared to conventional catalytic systems.

EXAMPLE 7

TABLE 3

| Run | Catalyst | Feed Amine moles | Alcohol mole | Conversion mole % | Yield % MEA | Yield % DMEA | Yield % DEMA | % Selectivity MEA | % Selectivity DMEA | % Selectivity DEMA |
|---|---|---|---|---|---|---|---|---|---|---|
| 1 | $La_2(HPO_4)_3$ | EA(1) | MEOH(1) | 57 | 27 | 25 | — | 47 | 44 | — |
| 2 | " | DEA(1) | MEOH(1) | 59 | — | — | 39 | — | — | 66 |

The above results show that the product mixture is not thermodynamically limited but kinetically controlled. Notice in Run 1 that essentially no monoalkyla- Synthesis of N-Ethyl Morpholine A 0.5 mole portion of diethylene glycol and 1 mole of monoethylamine were charged to a 300 ml, stirred, stainless steel autoclave. Approximately 5 grams of lanthanum hydrogen phosphate were charged to the reaction vessel. The reactor was then pressurized to 960 psig, and the temperature increased to 310° C. After about 2½ hours at 310° C., the pressure had risen to 1160 psig. The reaction was then terminated by cooling the contents and recovering the product. Gas chromatographic analysis showed that the main product was N-ethyl morpholine. Percent conversion based upon diethylene glycol was about 50% with approximately 75% selectivity to N-ethyl morpholine. This example proceeds via an initial intermolecular and subsequent intramolecular condensation reaction.

EXAMPLE 8

Intramolecular Condensation of Alkanolamine

The reaction of monoethanolamine (MELA) with itself was carried out by charging monoethanolamine as a 1:1 volume/volume mixture with tetraglyme to a tubular reactor containing approximately 6 grams of lanthanum dihydrogen phosphate. The reactor system was essentially the same as used in Example 2. The reaction was carried out at an LHSV of 1 (based upon MELA feed only) at a temperature of 318° C. and atmospheric pressure. The conversion was about 77% based upon MELA.

The product slate comprised approximately 27.3% piperazine, 0.8% aminoethylethanolamine, 33.1% aminoethyl piperazine, 27.6% bis-aminoethyl piperazine, and 9.5% piperazino ethylethylene diamine.

EXAMPLE 9

Preparation of Methoxyethoxyethyl Piperidine

The reaction of 2-methoxyethoxyethanol and piperidine in a feed molar ratio of 2:1, respectively, was carried out in accordance with the general procedure described in Example 8. Table 5 provides results the condensation reaction and process conditions.

TABLE 5

| ETHER PRODUCTION WITH LANTHANUM CATALYST[a] | | | | | |
|---|---|---|---|---|---|
| | | | % SELECTIVITY | | |
| LHSV (hr$^{-1}$)[b] | T (°C.) | CONVER- SION (%)[c] | 2-METH- OXYETH- YLPI- DINE | 1,2-BISPIPERI- DINOETHANE | x[f] |
| 1.0 | 300 | 18.04 | 41.65 | 50.29 | 8.06 |
| 2.0 | 300 | 14.92 | 45.88 | 42.22 | 12.20 |
| 2.0 | 300 | 22.63 | 42.40 | 51.29 | 6.31 |

[a]All experiments used lanthanum dihydrogen phosphate as catalyst.
[b]Based on 2-(2-methoxyethoxy)ethanol and piperidine; a 2:1 mole ratio of 2-(2-methoxyethoxy)-ethanol to piperidine was used in all experiments.
[c]Based on 2-(2-methoxyethoxy)ethanol; calculated as an area percent based on data.
[d]Area percent in the product, on a feedstock-free, water-free, area-normalized basis.
[e]Area percent in the product on a feedstock-free, water-free, area-normalized basis.
[f]Area percent of unknown products (x) on a feedstock-free area-normalized basis.

EXAMPLE 10

Preparation of TEDA

A feedstock prepared from ethylene glycol (EG), 1.865 weight parts, piperazine (PIP), 9.858 parts., an inert internal standard for gas chromotographic analysis, 1.865 parts triglyme, and 84.991 weight parts water, was pumped at a rate of 20 ml./hr. into a plug flow reactor containing a mixture of 5 cc of a lanthanum or praseodymium dihydrogen phosphate catalyst and quartz, both sieved to a 12 to 18 mesh size and intimately mixed before being charged. The reactor was a stainless steel tube having a length of about 18 inches, a ½ inch outside diameter and a wall thickness 0.035 inch. The reactor tube was oriented in a vertical direction and heated by an 18 inch long electric furnace into which the tube was inserted. A thermocouple was inserted into the reactor tube to monitor the temperature at the bottom of the catalyst bed. The system was operated at atmospheric pressure. The effluent was collected in a glass round-bottomed flask fitted with a water cooled condenser. The reactor system was brought on-stream by flowing ammonia over the catalyst at 3.0 g./hr. while heating the reactor to the desired operating temperature. When at the reaction temperatue, the ammonia was turned off and the feedstock pump turned on. After being on-stream for several hours at the desired temperature, samples were taken for analysis by gas-chromatography. Table 6 sets forth the results.

TABLE 6

| REACTION OF ETHYLENE GLYCOL AND PIPERAZINE OVER LANTHANIDE PHOSPHATES[a] | | | | | | | | | | | | |
|---|---|---|---|---|---|---|---|---|---|---|---|---|
| EXAM # | Cat.[b] | Temp. °C. | % Conv. E.G. | % Conv. PIP | WT %[c] | | | | | Unknowns Non.-Vol. | % Yield[d] to TEDA | % SEL[e] to TEDA |
| | | | | | EG | PIP | TEDA | HEP | BHEP | Vol. | | | |
| 1 | A | 300 | 79.9 | 19.2 | 3.20 | 68.0 | 15.6 | 0.6 | 0.3 | 2.8 | 9.6 | 54.5 | 68.0 |
| 2 | A | 320 | 87.1 | 41.0 | 2.05 | 49.6 | 17.7 | 0.5 | 0.3 | 6.7 | 23.2 | 61.4 | 70.5 |
| 3 | B | 300 | 79.3 | 12.9 | 3.30 | 73.3 | 12.6 | 0.5 | 0.9 | 1.3 | 8.1 | 43.9 | 55.4 |
| 4 | B | 320 | 94.9 | 53.3 | 0.82 | 39.2 | 20.1 | 0.4 | 0.3 | 2.8 | 36.4 | 70.1 | 73.9 |

[a]All experiments were conducted as described in Example 1.
[b]Catalyst A is a praseodymium dihydrogen phosphate catalyst. Catalyst B is a lanthanum dihydrogen phosphate catalyst.
[c]Wt % based on water and triglyme (internal standard) free basis.
[d]% Yield $= \frac{\text{Wt \% TEDA}/112}{\text{Wt \% EG}/62} \times 100$
[e]% Sel $= \frac{\text{Wt \% TEDA}/112}{(\text{Wt \% EG in feed} - \text{Wt \% EG in Prod})/62} \times 100$ As can be seen from Table 6 Runs 1-4 as the conversion of EG increases, the yield to TEDA increases but the conversion of PIP is progressively decreasing.

EXAMPLE 11

A feedstock mixture of 25.5 weight parts diethylene glycol, 48.8 weight parts ammonia, and 25.6 weight parts tetraglyme, was pumped at a rate of 9.3 ml/hr. into the reactor described in Example 10 which was maintained at 250 psig by the use of a back pressure regulator in the exit stream. The reactor was charged with a mixture of 5 cc quartz and 5 cc of the lanthanide dihydrogen phosphate catalyst which were both sieved to 12–18 mesh and intimately mixed before charging. The reactor was brought on-stream by charging anhydrous ammonia downflow over the catalyst at 3.0 g/hr while heating the reactor to the desired temperature. When the desired temperature was reached, the ammonia was turned off, and the feedstock was introduced downflow in its place. After maintaining the feedstock flow for several hours, the effluent was analyzed by gas chromatography. The results are reported in Table 7.

TABLE 7
REACTION OF DIETHYLENE GLYCOL AND AMMONIA OVER LANTHANIDE PHOSPHATE CATALYSTS

| RUN # | CAT[a] | TEMP. °C. | % DEG CONV. | NORMALIZED WT %[b] | | | | | | | | YIELD % MOR | SEL % MOR |
|---|---|---|---|---|---|---|---|---|---|---|---|---|---|
| | | | | DEG | MOR | DEGA | DIOX | AEM | MDEG | MDGA | DME | BMDEG | | |
| 1 | A | 290 | 36.4 | 68.9 | 11.6 | 1.0 | 5.5 | — | 3.9 | 1.6 | 4.2 | 3.4 | 13.0 | 35.9 |
| 2 | B | 260 | 45.3 | 60.8 | 13.3 | 3.6 | 4.7 | 6.3 | 5.8 | 2.5 | 1.9 | 1.1 | 14.6 | 32.3 |
| 3 | B | 275 | 51.9 | 54.5 | 17.5 | 3.8 | 2.0 | 8.2 | 6.6 | 3.4 | 2.0 | 2.0 | 18.8 | 36.2 |

[a] A = Praseodymium dihydrogen phosphate
B = Lanthanum dihydrogen phosphate
[b] Wt % exclusive of water and ammonia.
CAT refers to catalyst, DEG to diethylene glycol, MOR to morpholine, DEGA refers to 2-aminoethoxyethanol. DIOX refers to dioxane, AEM refers to aminoethylmorpholine glycol, MDGA refers to 2-(2-aminoethoxy) ethylmorpholine DME refers to (1,2 dimorpholine ethane and BMDEG refers to bis-morpholine diethylene glycol. One interesting aspect of the reaction is that the DEGA is produced in lower amounts than expected, i.e., based upon results reported with hydrogenation-dihydrogenation catalysts.

What is claimed is:

1. In a process for the synthesis of an organic amine by the condensation of a hydroxy composition with ammonia or a primary or secondary amine said condensation being effected in the presence of a phosphorus-containing compound as a catalyst, the improvement which comprises:
   effecting condensation between
   (a) an organic hydroxy composition represented by the formula: $R(OH)_x$ where R is a saturated aliphatic radical having from 1 to 6 carbon atoms, an olefinic radical having from 3 to 6 carbon atoms, aliphatic ether having from 4 to 8 carbon atoms or aminoaliphatic where the aliphatic portion has from 2–6 carbon atoms: and x is 1 when R is methyl and 1 or 2 when R, has 2 or more carbon atoms and
   (b) an amino composition represented by the formula: $R_1R_2NH$
   where $R_1$ and $R_2$ are each selected from hydrogen, a saturated aliphatic radical having from 1 to 4 carbon atoms, an olefinic radical having 3–6 carbon atoms, hydroxyalkyl where the alkyl portion has from 2 to 6 carbon atoms, and aliphatic ether having from 4–8 carbon atoms or $R_1$ and $R_2$ are are combined with the nitrogen to form a heterocyclic group having 4 to 10 carbon atoms; except where compositions (a) and (b) are defined by the same formula and then only one of said compositions is required; and
   Employing as said phosphorus-containing compound a catalyst comprising a rare earth metal hydrogen phosphate.

2. The process of claim 1 wherein said rare earth metal hydrogen phosphate comprises a lanthanum hydrogen phosphate.

3. The process of claim 2 wherein x in said organic hydroxy composition is 1.

4. The process of claim 3 wherein R in said organic hydroxy composition is a saturated aliphatic radical having from 1–6 carbon atoms.

5. The process of claim 3 wherein said organic hydroxy compound is an alkanol having from 1 to 4 carbon atoms or an alkanolamine having from 1 to 4 carbon atoms and said amino compound is a primary or secondary amine and $R_1$ and $R_2$ are each selected from hydrogen or saturated aliphatic radical having from 1 to 4 carbon atoms and the product is a symmetrical or unsymmetrical amine.

6. The process of claim 3 wherein $R_1$ and $R_2$ in said amino compound are hydrogen.

7. The process of claim 3 wherein $R_1$ is hydrogen or and $R_2$ is a saturated aliphatic radical.

8. The process of claim 5 wherein said organic hydroxy composition is methanol and said amino compound is methylamine or ethylamine.

9. The process of claim 3 wherein said amino composition $R_1$ and $R_2$ are joined to form a heterocyclic group having 4 to 10 carbon atoms.

10. The process of claim 9 wherein said amino compound is piperazine.

11. The process of claim 9 wherein said amino compound is morpholine.

12. The process of claim 2 wherein R is $C_2$ or greater in said organic hydroxy compound and x is 2.

13. The process of claim 12 wherein said organic hydroxy compound is diethylene glycol.

14. The process of claim 13 wherein said amino compound is ammonia or an alkylamine having from 2 to 3 carbon atoms.

15. The process of claim 12 wherein said organic hydroxy composition is ethylene glycol.

16. The process of claim 2 wherein said organic hydroxy compound is an alkanolamine and said amino compound is morpholine.

17. The process of claim 16 wherein said organic hydroxy compound is dimethylethanolamine.

18. The process of claim 2 wherein said organic hydroxy compound is an alkoxy alkanol having from 4 to 8 carbon atoms.

19. The process of claim 18 wherein $R_1$ and $R_2$ of said amino composition are combined to form a heterocyclic group.

20. The process of claim 19 wherein said amino compound is piperidine, piperazine or morpholine.

21. The process of claim 20 wherein said rare earth hydrogen phosphate comprises a lanthanum hydrogen phosphate.

22. The process of claim 1 wherein in said amino composition $R_1$ and $R_2$ are combined with the nitrogen to form a heterocyclic group.

23. The process of claim 2 wherein (a) and (b) are hydroxy ethyl piperazine.

24. The process of claim 2 wherein (a) and (b) are 2-aminoethoxyethanol.

25. The process of claim 2 wherein said hydroxy compound is allyl alcohol and said amine compound is ammonia or an alkylamine having from 1 to 4 carbon atoms.

26. The process of claim 2 wherein said organic hydroxy and amino compound is an alkanol amine having from 2–4 carbon atoms.

27. The process of claim 26 wherein said alkanolamine is monoethanolamine.

* * * * *